United States Patent [19]

Engelbach et al.

[11] 4,255,285
[45] Mar. 10, 1981

[54] COATED CATALYSTS AND THEIR PREPARATION

[75] Inventors: Heinz Engelbach, Limburgerhof; Harry Hoffmann, Ludwigshafen; Peter Palm, Gerolsheim; Karl Sommer; Michael J. Sprague, both of Ludwigshafen, all of Fed. Rep. of Germany

[73] Assignee: BASF Aktiengesellschaft, Fed. Rep. of Germany

[21] Appl. No.: 23,359

[22] Filed: Mar. 23, 1979

[30] Foreign Application Priority Data

Apr. 3, 1978 [DE] Fed. Rep. of Germany ....... 2814262

[51] Int. Cl.³ .............................................. B01J 23/22
[52] U.S. Cl. .............................. 252/443; 252/455 R; 252/456; 252/461; 252/464; 252/467; 252/471; 252/472; 252/475; 252/476
[58] Field of Search .................. 252/461, 443, 455 R, 252/456, 464, 467, 472, 475, 476, 471; 260/369

[56] References Cited

U.S. PATENT DOCUMENTS 4,151,182   4/1979   Engelbach et al. ............. 252/461 X

FOREIGN PATENT DOCUMENTS

| | | |
|---|---|---|
| 1934063 | 6/1972 | Fed. Rep. of Germany . |
| 2025430 | 1/1973 | Fed. Rep. of Germany . |
| 2224016 | 8/1973 | Fed. Rep. of Germany . |
| 2028424 | 9/1973 | Fed. Rep. of Germany . |
| 2160781 | 9/1973 | Fed. Rep. of Germany . |
| 2135421 | 12/1973 | Fed. Rep. of Germany . |
| 2122664 | 8/1974 | Fed. Rep. of Germany . |
| 2060215 | 2/1975 | Fed. Rep. of Germany . |
| 2050797 | 7/1975 | Fed. Rep. of Germany . |
| 2232453 | 7/1975 | Fed. Rep. of Germany . |
| 2314695 | 7/1975 | Fed. Rep. of Germany . |

*Primary Examiner*—W. J. Shine
*Attorney, Agent, or Firm*—Keil & Witherspoon

[57] ABSTRACT

Novel coated catalysts and a process for their preparation by atomizing a mixture of water and a vanadium-V compound, with or without other metal compounds, and applying this mixture to carrier particles which are themselves in motion, drying the coating and subjecting the catalyst particles, which are themselves in motion, to repeated brief treatment with a flame or plasma, followed by rapid cooling, defined temperatures and rates of coating being employed. The catalysts may be used with advantage for the preparation of anthraquinones by oxidation of indans.

17 Claims, No Drawings

COATED CATALYSTS AND THEIR PREPARATION

The present invention relates to novel coated catalysts and to processes for their preparation by atomizing a mixture of water and a vanadium-V compound, with or without other metal compounds, and applying this mixture to carrier particles which are themselves in motion, drying the coating and subjecting the catalyst particles, which are themselves in motion, to repeated brief treatment with a flame or plasma, followed by rapid cooling, defined rates of coating being employed.

The use, in catalytic reactions, of coated catalysts which consist of carriers, for example in the form of beads, tablets or extrudates, the surface of which is covered with a coating of a catalytic material, is known. The carriers used are non-porous or only slightly porous inert materials. These carriers are coated with the active material by stirring the catalytic materials with water or an organic solvent to form a paste, and coating the carrier, which may for example be kept agitated in a coating drum, by gradual addition of the paste. This method gives coated catalysts wherein the coating is from about 0.02 to 4 millimeters thick. The catalysts coated with the active components must subsequently be heated to elevated temperatures for a substantial time.

German Pat. No. 2,025,430 discloses that coated catalysts consisting of a carrier, with a layer of catalytic material applied thereto, can be produced by applying the catalytic material to the carrier by a plasma spraying or flame spraying process. The patent states that the carrier particles are advantageously spherical in order to minimize pressure losses in the reactor. The particles can, for example, be produced in a pelletizing drum. A precondition of the applicability of the process is that at least one of the principal components should be fusible at the working temperature of the flame-spraying torch, which is operated as an oxyacetylene torch, or of the plasma torch. The process is carried out by introducing the active components, or the substances which at the working temperature of the torch can be decomposed to the desired oxidic catalytic compounds, into the flame or plasma jet in the conventional manner. The flame or plasma jet is directed onto the particles to be coated, which are preferably kept in motion, for example in a rotating drum. The catalysts thus produced are used, for example, for the oxidation of indans, in which case the catalytic coatings applied to the carrier particles consist of vanadium pentoxide or of molybdenum oxide and/or tungsten oxide.

The Examples show that the catalytic activity of the coated catalysts can be substantially increased compared to that of conventionally produced coated catalysts, specifically by the fact that the catalytic material, for example vanadium pentoxide powder, is sprayed as a fused mass, by a flame-spraying torch or plasma torch, onto the carrier, after which the catalyst may or may not be calcined for one hour at 650°–700° C. The above statement is based on the fact that the Comparative Example refers to the application of the catalytic material onto the carrier beads by means of an atomizer at 200° C.; the coated beads are then heated in air for one hour at each of the following temperatures: 200°, 300°, 500° and 700° C. The catalysts obtained by this conventional method of applying the coating by atomizing give a yield of only 13.8 percent as compared to the yield of 45 percent resulting from the process described in German Pat. No. 2,025,430.

Though the above process gives better results, in particular in respect of yield of end product, than earlier processes, it is still not entirely satisfactory. In the plasma spraying and flame spraying processes, the active material must be fed to the torch pneumatically. This requires a free-flowing material, and can only be carried out entirely trouble-free if the particle size of the active material is from about 50 to 200 $\mu$m and if the individual particles are substantially spherical. This particle shape and particle size distribution are difficult to achieve on an industrial scale. It is best achieved by fusing and then spraying the active material by means of a stream of gas, the sprayed material of particle size $<50\mu$ and $>200\mu$ being recycled. A disadvantage of this method of producing the optimum particle size distribution is the high energy consumption and the expensive gas purification, by washing and electrostatic precipitators, which becomes necessary because of the toxicity of, for example, vanadium. However, similarly expensive gas purification is required in the case of flame spraying, since only from 50 to 70 percent of the active material fed to the torch is fused onto the carrier beads; the remainder must be recovered from the off-gas.

German Pat. Nos. 1,934,063, 2,028,424, 2,050,797, 2,060,215, 2,122,664, 2,135,421, 2,160,781 and No. 2,314,695 and German Laid-Open Application DOS No. 2,224,016 disclose that indans can advantageously be oxidized in the presence of vanadium pentoxide and/or vanadates of other elements. The above publications describe the preparation of the catalysts by precipitating a solution of ammonium vanadate with the appropriate metal salts, for example a solution of antimony tartrate, ferric nitrate, cesium nitrate, rubidium nitrate or titanium-III oxalate, and filtering and drying the metal vanadate precipitate, or by evaporating a solution of ammonium vanadate together with the appropriate metal salt. If the carrier is added before or during the precipitation, the metal vanadate at the same time becomes finely distributed over the carrier. It is also possible to apply the solution or suspension of the vanadate to the carrier by impregnation or spraying. Further, it is possible to mix the dry or moist vanadate with the carrier, comminute the mixture if appropriate, and then convert the mixture to appropriate shaped particles, for example by means of an extruder. After drying, it may be advantageous to calcine the catalyst, for example at from 300 to 700° C. Vanadium pentoxide catalysts can for example be prepared by dissolving vanadium pentoxide in aqueous oxalic acid or hydrochloric acid, applying the solution to a suitable carrier, for example titanium dioxide or steatite, drying the carrier and, if appropriate, calcining the material. Solutions of ammonium vanadate in water may be used similarly. However, it is specifically pointed out, for example as early as in German Pat. No. 2,028,424, that a particularly advantageous method of preparing the catalysts proves to be flame spraying or plasma spraying onto spherical carriers, for example by the process described in German Pat. No. 2,025,430. The above compounds of other elements can be mixed mechanically with the vanadium pentoxide to be applied by flame spraying or with a compound which on heating is converted to vanadium pentoxide, for example vanadic acid. However, it is also stated to be advantageous first to prepare a homogeneous solution which contains the metals to be applied.

From this solution the compounds to be applied can be obtained by, for example, evaporation. As the Examples, e.g. those described in German Pat. No. 2,028,424 show, a catalytic material is as a rule prepared from compounds of the above elements and is then applied to the carrier by flame spraying, using the method of German Pat. No. 2,025,430. German Pat. Nos. 2,050,797, 2,122,664 and No. 2,135,421 and German Laid-Open Application DOS No. 2,224,016 teach that an advantageous method is to apply the active material to the carrier by flame spraying or plasma spraying and then to calcine the catalyst at from 450 to 650° C., preferably from 500° to 600° C., for from 1 to 24 hours.

We have found novel coated catalysts, comprising a non-porous or slightly porous carrier and a layer of catalytic material, containing vanadium-V compounds, applied thereto, which are obtained by atomizing a mixture of water and vanadium-V compound with or without other metal compounds, and applying this mixture as a coating onto carrier particles which are themselves in constant motion, at from 20° to 90° C. and with a rate of application of from 0.001 to 0.02 part by weight of solids per part by volume of carrier beads per minute, then drying the coated catalysts thus obtained and, by flame heating or plasma heating of the coated catalyst particles which are themselves in constant motion, repeatedly heating all parts of the catalyst surface briefly to above 700° C. and cooling to below 650° C.

Further, we have found that coated catalysts comprising a non-porous or only slightly porous carrier and a layer of catalytic material, containing a vanadium-V compound, applied thereto can be prepared advantageously by atomizing a mixture of water and a vanadium-V compound, with or without other metal compounds, and applying this mixture as a coating onto carrier particles which are themselves in constant motion, at from 20° to 90° C. and with a rate of application of from 0.001 to 0.02 part by weight of solids per part by volume of carrier beads per minute, then drying the coated catalysts thus obtained and, by flame heating or plasma heating of the coated catalyst particles which are themselves in constant motion, repeatedly heating all parts of the catalyst surface briefly to above 700° C. and cooling to below 650° C.

Further, we have found that the coated catalysts can advantageously be used for the preparation of anthraquinones by oxidation of indans of the formula

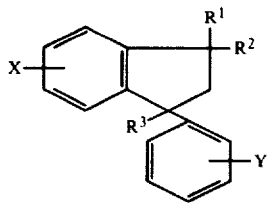

I where $R^1$, $R^2$ and $R^3$ may be identical or different and each is alkyl, $R^1$ and/or $R^3$ may in addition also each be hydrogen, and X and Y may be identical or different and each is halogen or hydrogen, by means of oxygen in the gas phase in the presence of a vanadium-V compound and, if desired, one or more compounds of other metals.

The invention is based on the observation that very efficient vanadium coated catalysts, which are particularly suitable for the oxidation of indans to anthraquinones, owe their efficiency not only to their composition in respect of the added elements, and their proportion by weight relative to vanadium, essentially also to a specific combination of characteristics of the catalyst structure, which in particular are determined by the following factors; application of a suspension at a particular rate of application and application temperature, with the carrier particles being themselves in rolling motion during the application; exposure of the catalyst, for a selected and brief period, to a very high temperature which causes the vanadium pentoxide and, where relevant, the additional metal oxides and metal vanadates, within the catalystic material to fuse entirely or partially during this period; implementation of this heat treatment in the form of a flame spraying treatment or plasma spraying treatment; rapid cooling under specific temperature conditions; and repeated heating and cooling of the catalyst surface. Compared to the conventional processes, the process of the invention produces coated catalysts, containing vanadium pentoxide, more simply and more economically. If the catalysts are used for the oxidation of indans, the corresponding anthraquinones are obtained in good yield and high purity. It becomes unnecessary to convey the active material through the flame-spraying apparatus, since the latter is only used for briefly heating the catalyst coating; accordingly, the free-flowing character, particle size and structure of the active material are relatively far less important, or even immaterial. For example, it is possible to use particle sizes of the active material of from 50 micrometers to less than 1 micrometer, whilst such sizes are unsuitable for the flame spraying process. Special preparation of the active particles, for example by fusing and spraying the active material in a stream of gas, is avoided, energy is saved and additional cleaning operations carried out on the off-gas become unnecessary. Since the active material is not atomized by the flame-spraying apparatus, the off-gas no longer carries the corresponding proportion of active material, and it is therefore no longer necessary to separate off, and recycle, such material. The preparation of the catalyst is therefore simpler, less prone to faults, more economical and environmentally less polluting, particularly when carried out on an industrial scale. All these advantageous results obtained according to the invention are surprising in view of the prior art.

The active material used comprises one or more vanadium-V compounds, preferably vanadium pentoxide and/or vanadates. The vanadium-V compound can also be present in the catalyst as a mixture with the corresponding vanadium-IV compound. The vanadates can be monovanadates or polyvanadates, especially orthovanadates, pyrovanadates and metavanadates. Amongst the vanadates, those of elements of groups Ia, IIb, IIIa, IIIb, IVa, IVb, Va, Vb, VIa, VIb, VIIb and VIIIb of the periodic table, especially ammonium, potassium, thallium, boron, tellurium, cadmium, germanium, niobium, lead, rubidium, chromium, tungsten, uranium, arsenic, indium, cesium, zinc, molybdenum, iron, titanium, tin, antimony and manganese vanadate, are preferred. A mixture of vanadium-V compounds with oxides of elements of groups Ia, IIb, IIIa, IIIb, IVa, IVb, Va, Vb, VIa, VIb, VIIb and/or VIIIb of the periodic table (as given by D'Ans-Lax, Taschenbuch für Chemiker und Physiker, 3rd edition (1967), volume 1, page 63) can be used as the active material for the reaction, advantageous mixtures being those with the oxides of potassium, thallium, boron, tellurium, cadmium, germanium, niobium, lead, rubidium, chromium, tungsten, uranium, arsenic, indium, cesium, zinc, molybdenum, iron, titanium, tin, antimony and manganese.

Mixtures of vanadium-V compounds and additional compounds of elements which form vanadates and/or oxides under the reaction conditions may also be used, for example a mixture of one or more vanadium-V compounds and one or more compounds of elements of groups Ia, IIb, IIIa, IIIb, IVa, IVb, Va, Vb, VIa, VIb, VIIb and/or VIIIb of the periodic table, especially compounds of potassium, thallium, boron, tellurium, cadmium, germanium, niobium, lead, rubidium, chromium, tungsten, uranium, arsenic, indium, cesium, zinc, molybdenum, iron, titanium, tin, antimony and manganese.

Regardless of the composition of the compounds and of the valency of the metals in the compounds present in the active material, the atomic ratio, in the catalyst, of vanadium to the added elements of group Ia is from 2,000 to 0.5 atom of vanadium per atom of added element, whilst for group IIIa it is from 4,000 to 1 atom of vanadium per atom of added element, for group IVa it is from 2,000 to 0.1 atom of vanadium per atom of added element, for group Va it is from 2,000 to 1 atom of vanadium per atom of added element, for group VIa it is from 2,000 to 1 atom of vanadium per atom of added element, for group VIIb it is from 2,000 to 3 atoms of vanadium per atom of added element, for group VIIIb it is from 100,000 to 0.5 atom of vanadium per atom of added element, for group IIb it is from 2,000 to 3 atoms of vanadium per atom of added element, for group IIIb it is from 2,000 to 1 atom of vanadium per atom of added element, for group IVb it is from 2,000 to 0.1 atom of vanadium per atom of added element, for group Vb it is from 4,000 to 5 atoms of vanadium per atom of added element and for group VIb it is from 2,000 to 4 atoms of vanadium per atom of added element.

The compounds of the added elements can be chosen as desired; in general, the oxides, acids, bases, salts, for example carbonates, bicarbonates, oxalates, chlorides or nitrates, ammonium salts of metal-acid, and compounds of the added elements which during the preparation of the catalyst are converted to the corresponding oxides and/or vanadates, can be employed. The addition of antimony and thallium is particularly advantageous. The preferred atomic ratios are from 30,000 to 10, especially from 6,000 to 25, atoms of vanadium per atom of thallium and from 8,000 to 3, especially from 1,600 to 8, atoms of vanadium per atom of antimony. The compounds added advantageously have a melting point of less than 1,200° C. Such compounds are particularly preferred in cases where a substantial amount of the added element is present in the catalyst. Where necessary, a plasma torch should be used in the case of relatively high-melting compounds. In that case, it is advantageous to avoid partial reduction of vanadium-V to vanadium-IV, since the compounds of the latter have higher melting points.

Examples of suitable added compounds are potassium chloride, potassium carbonate, boron trioxide, thallium nitrate, boric acid, potassium hydroxide, antimony trioxide, antimony tetroxide, antimony pentoxide, hydrated antimony trioxides, hydrated antimony pentoxides, potassium nitrate, potassium bicarbonate, potassium oxalate, potassium formate, germanium oxide, ammonium molybdate, niobium nitrate, tungsten nitrate, uranium acetate, indium nitrate, uranium dioxide, thallium acetate, thallium carbonate, thallium vanadate, ammonium borate, cesium carbonte, cesium nitrate, cesium bicarbonte, cesium oxalate, cesium formate, cesium acetate, cesium hydrogen tartrate, zinc sulfate, cadmium carbonate, zinc oxide, zinc nitrate, zinc hydroxide, cadmium oxide, cadmium nitrate, zinc oxalate, zinc formate, cadmium acetate, zinc carbonate, cadmium sulfate, cadmium hydroxide, zinc acetate, oxyacids of tellurium, ammonium tellurate, tellurium dioxide, potassium tellurite, tellurium trioxide, cesium tellurate, potassium tellurate and thallium tellurate.

In addition to one or more vanadium-V compounds, the catalyst may contain one or more added compounds, for example oxides, of other elements, preferably the above compounds, for example oxides, of the above elements. Not only combinations of 2 compounds, but combinations of vanadium-V with compounds of 2, 3, 4 or 5 other elements are advantageous. The combination of compounds of vanadium, antimony and thallium is particularly preferred. Salts of the above metals with oxy-acids formed from appropriate metals from amongst those mentioned above, such as tungsten, may also be used; for example, iron tungstate, cesium tellurate and rubidium tungstate are suitable. If desired, vanadium can be present exclusively in the form of vanadates of the preferred metals.

The carrier particles used are non-porous or only slightly porous materials, for example silica compunds such as silicates, e.g. sodium aluminum silicate, magnesium silicate, calcium aluminum silicate, bleaching earths, fuller's earth, clays, kaolin, meerschaum, allophanes, zeolites, montmorillonite, pumice, Florida earth, quartz, asbestos, mullite, steatite and bentonite; precipitated silica, silica gel, kieselguhr and silicon carbide; α- and γ-aluminum oxides and aluminum hydroxides, e.g. corundum, γ-alumina, hydrargillite, boehmite and bauxite; aluminum silicates, e.g. andalusite; titanium dioxide, zirconium dioxide, tin dioxide, thorium dioxide, magnesia and zinc oxide. Preferred carriers are mullite, silicon carbide, α-aluminum oxide and especially steatite. It is also possible to use the oxygen-containing compound of an added element, for example titanium-IV oxide or iron-III oxide, simultaneously as the carrier for the catalytic material. The shape and size of the carrier particles can be selected within a wide range; for example, tableted, granular or particulate carriers, extrudates or pellets may be used, spherical or annular carrier particles, suitably with an average diameter of from 2 to 10 millimeters, being advantageous. The catalytic material (vanadium-V compounds with or without added compounds) is advantageously applied to the carrier in an amount of from 0.02 to 0.5, preferably from 0.15 to 0.25, part by weight per part by volume of carrier.

As a rule, the active material (vanadium-V compounds with or without compounds of added elements) is atomized in the form of an aqueous suspension, advantageously of from 7 to 70 percent strength by weight, preferably of from 20 to 40 percent strength by weight. The dispersing device used is preferably an atomizer and advantageously a nozzle, for example an injector mixer, jet mixer, vortex chamber nozzle, eccentric nozzle, bundle nozzle, centrifugal pressure nozzle, slit nozzle, flat jet nozzle, hollow nozzle or spiral nozzle and especially an atomizing nozzle, two-fluid nozzle, rotary atomizer, impact nozzle, solid cone nozzle, rotary atomizer disks with vanes, rotary atomizer disks with nozzles, Schlick nozzles, Siccatom nozzles or hollow cone nozzles. The carrier, in the form of the particles mentioned above, is itself in constant motion during application of the coating. As a rule, this constant motion of the carrier itself is achieved by means of rotating vessels with disk-shaped bottoms, for example rotary dishes, rotary drums, coating dishes, impregnating drums or coating drums, by means of helical ribbon impellers of by means of mixers on the bottom of which the carrier particles are present. The angle to the horizontal depends on the apparatus used; if coating dishes or rotary dishes are used, the bottom of the vessel, on which the carrier particles are present, is set at an angle to the horizontal, advantageously of from 30° to 70°, preferably from 40° to 50°, and in this way, in addition to the motion of the particles imposed by the rotating bottom, a constant and substantial motion of the particles themselves is additionally provided, due to gravity. Angular particles will therefore, during this motion, constantly tumble over, whilst round particles, especially rings or beads, will execute a rolling motion and possibly a spinning motion. Since the particles constantly mutually hinger one another from executing a linear motion, as a result of striking one another, all the above moments of motion result in a rolling overall motion of the carrier particles, such as can also be observed, for example, when coating loose material in a coating drum. For this reason, particles which roll relatively easily, such as rings and especially beads, are preferred. A particular difference between the process according to the invention and impregnation and coating with solutions is that in the process according to the invention the material is applied in the form of a mixture of active material and water, with the particles of material being completely or partially undissolved in the water and accordingly forming a suspension. During atomizing, the suspension is advantageously at from 10° to 90° C., whilst the temperature during application of the active material, advantageously measured as the temperature within the loose material, is advantageously from 20° to 90° C., especially from 40° to 70° C. The term loose mass means, here and in the text which follows, the total mass of particles to be coated or the total mass of the coated catalyst, and the surface of this total mass is referred to as the loose mass surface. The atomized suspension is sprayed onto the rolling carrier particles at a speed such that from 0.001 to 0.02, preferably from 0.005 to 0.015, part by weight of solid is applied per part by volume of carrier beads per minute. As a result of the constant rolling motion, a relatively uniform layer of active material is produced at the same time. As a result of the rotary motion of the apparatus, the carrier particles are raised by frictional forces exerted by the walls, and by baffles, if any, and then roll down under gravity on the surface of the loose mass and form the new surface thereof. During coating, the apparatus is advantageously filled with carrier particles to the extent of from 20 to 80 percent by volume; the speed of rotation of the bottom of the vessel depends on the apparatus used and on its size and is in general from 2 to 70 rpm.

Thereafter, the particles are dried through direct or indirect heating, advantageously until the temperature of the loose mass has reached 100°–110° C., and advantageously in the same rotating vessel or a similar rotating vessel, preferably a rotating dish or rotating drum. After the drying process, the residual amount of water in the active material is advantageously from 1 to 10 percent by weight, based on the active material (calculated as solids). Advantageously, the drying is carried out entirely or partially whilst the coating is being applied, for example by blowing in air or an inert gas, advantageously at from 100° to 300° C. The flame heating or plasma heating of the coated catalysts is carried out by means of a gas torch or plasma torch directed towards the loose mass surface of the particles, with the individual coated catalysts also being contained in rotary vessels, suitably in the same rotary vessels, advantageously rotary dishes, impregnating drums or coating drums. The above data in respect of the angle of the vessel bottom to the horizontal, the degree of filling and the rotation of the bottom represent advantageous conditions, and the temperature within the loose mass is advantageously below 650° C., especially from 650° to 300° C., more especially still from 650° to 500° C. and preferably from 650° to 600° C. As a result of the rolling motion of the loose mass, the flame jet or plasma jet only briefly impinges on each part (segment) of the surface of each individual catalyst particle, heats this segment to above 700° C., preferably to from 700° to 3,000° C., especially from 700° to 1,500° C. and more especially from 700° to 1,000° C.("heating temperature"), and keeps it briefly at this temperature, after which the heated segments are again displaced by other segments of other coated catalyst particles, which now in turn are brought to the heating temperature according to the invention. Advantageously, the duration of bringing the individual segments from the temperature within the loose mass to the heating temperature and keeping them at this temmperature is from 0.1 to 1 second. The heated segments of the surface of the coated catalyst particles which have been displaced from the heating zone rapidly reassume the temperature prevailing within the loose mass. Each segment of the coated catalyst particles advantageously cools, after having been heated, within from 0.1 to 1 second to the cooling temperature, ie. to the temperature within the loose mass, and remains at this temperature until it undergoes the next heating step. The rolling motion thus subjects all the segments of all the catalyst particles repeatedly to the flame jet or plasma jet treatment and the subsequent rapid cooling. Hence, preferred shapes of the coated catalyst particles are those which favor a uniform rolling motion, ie. round shapes, especially circular, cylindrical and advantageously spherical or approximately spherical coated catalyst particles (for example pellets) are particularly advantageous. Advantageously, from 10 to 1,000, preferably from 20 to 200, kg of coated catalyst particles are employed both in the coating step and in the step of heating by flame or plasma treatment, and in accordance therewith the total treatment time of the coated catalysts with the gas torch or plasma torch is from 2 to 60 minutes, preferably from 10 to 30 minutes. The flame of the gas torch can be produced from, for example, methane/oxygen, propane/oxygen or, advantageously, acetylene/oxygen or natural gasoxygen. Instead of oxygen, air can also be used. It is advantageous to employ vessel bottom diameters—when using rotary dishes—of from 0.5 to 5 meters, especially from 0.5 to 2 meters, distances of the torch from the surface of the loose mass of from 2 to 70, preferably from 30 to 60, centimeters, and flame temperatures of from 700° to 2,000° C.

The coated catalysts thus obtained are advantageously used for the manufacture of anthraquinones by oxidation of indans, preferably by the methods described in the patents cited earlier, and exhibit a high activity and high selectivity in such processes. In particular, it is advantageous to use the above preferred vanadium compounds and, if desired, the preferred additional metal compounds, and the above ratios of vanadium to other metal compounds.

Where 1-methyl-3-phenyl-indan is used, the reaction can be represented by the following equation:

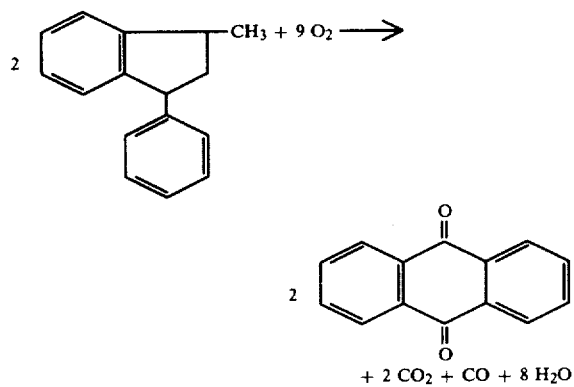

The indans used as starting materials I can be prepared by dimerization of substituted or unsubstituted styrenes, for example by the methods described in the publications cited earlier or in Rabjohn, Organic Syntheses, Collective Volume IV (John Wiley Inc., New York 1963), pages 665 et seq. Preferred indans I and accordingly preferred anthraquinones of the formula

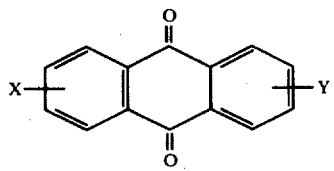

are those where $R^1$, $R^2$, and $R^3$ are identical or different and each is alkyl of 1 to 4 carbon atoms, $R^1$ and/or $R^3$ may in addition also each be hydrogen, and the radicals X and Y are identical or different and each is bromine, fluorine or especially hydrogen or chlorine. Examples of suitable indans I are 1-methyl-3-phenyl-indan, 1,3-dimethyl-3-phenyl-indan, 1,1,3-trimethyl-3-phenyl-indan, 1-propyl-3-phenyl-indan, 1-isobutyl-3-phenyl-indan, 3-o-chlorophenyl-1-methyl-indan, 3-m-chlorophenyl-1-methyl-indan, -b 3-p-chlorophenyl-1-methyl-indan, 3-o-bromophenyl-1-methyl-indan, 3-m-bromophenyl-1-methyl-indan, 3-p-bromophenyl-1-methyl-indan, 3-m-chlorophenyl-1-methyl-4-chloro-indan, 3-m-bromophenyl-1-methyl-4-bromo-indan, 3-o-chlorophenyl-1-methyl-7-chloro-indan, 3-o-bromophenyl-1-methyl-7-bromo-indan, 3-m-chlorophenyl-1-methyl-6-chloro-indan, 3-m-bromophenyl-1-methyl-6-bromo-indan, 3-p-chlorophenyl-1-methyl-5-chloro-indan and 3-bromophenyl-1-methyl-5-bromo-indan.

The oxidation is as a rule carried out with an excess of oxygen. The use of a ratio from 15 to 400 moles of oxygen per mole of indan I above the stoichiometric amount is preferred. As a rule, oxygen is used in the form of air, but any mixtures of oxygen and gases which are inert under the reaction conditions, such as argon, steam, nitrogen and/or carbon dioxide, or flue gas, may also be used. Preferably, espeically in the case of 1-methyl-3-phenyl-indan, each cubic meter (S.T.P.) of air is charged with from 5 to 100, advantageously from 10 to 60, especially from 25 to 55, grams of starting material I. In the case of the halogenated 1-methyl-3-phenyl-indans, the amount is preferably from 5 to 100, advantageously from 20 to 70, especially from 30 to 60, grams of starting material I per cubic meter (S.T.P.) of air. In continuous operation, a suitable amount of starting material I to be oxidized per liter of catalyst per hour is from 20 to 2,000, preferably from 40 to 1,000, advantageously from 60 to 600, grams. The same amounts of starting material I, based on catalyst, are also used, as a rule, in batchwise operation.

The oxidation is as a rule carried out at from 200 to 500° C., preferably from 250 to 470° C., especially from 350 to 470° C., under atmospheric or superatmospheric pressure, batchwise or, preferably, continuously. This temperature is as a rule measured as the temperature of the cooling medium, for example of a potassium nitrate bath, and represents the tube wall temperature. The starting material I is, for example, oxidized as follows: the indan I is vaporized and mixed with a stream of air which is advantageously heated to 200°–400° C. It is also possible to saturate an oxygen-free part-stream of the reaction off-gases with the vapor of the starting material so as to obtain the desired concentration of indan I in the reaction mixture. The gas/vapor mixture is then passed through the catalyst bed in a reactor at the reaction temperature. Suitable reactors are tubular reactors cooled with a salt bath, fluidized bed reactors with built-in cooling elements, or multiple-bed reactors with intermediate cooling. The end product is then isolated from the reaction mixture in the conventional manner, for example by passing the gases, leaving the reactor, through one or more separators in order to free the anthraquinone from the greater part of the by-products. If desired, the end product can be purified, for example by passing the reaction mixture into water or dilute sodium hydroxide solutin and isolating the end product from the resulting solid residue by sublimation, or by dissolving the end product in an alkaline sodium dithionite solution, filtering off the unconverted starting material, then precipitating the end product from the filtrate by oxidation with air, and isolating the product. Preferably, the anthraquinone is isolated from the mixture of its vapor with a hot carrier gas in accordance with the process described in German Pat. No. 2,232,453, by treating the mixture of anthraquinone vapor and carrier gas, heated to at least 200° C., with an aqueous suspension of anthraquinone, which may or may not contain ammonia, at below the boiling point of water at the prevailing pressure.

The anthraquinones obtainable in accordance with the invention are valuable starting materials for the preparation of dyes and pesticides. Regarding their use, reference may be made to the publications cited earlier and to Ullmanns Encyklopädie der technischen Chemie, volume 3, pages 659–732. The mono- and dihaloanthraquinones can be converted by conventinal methods, entailing replacement of the halogen atoms by amino groups, to the corresponding aminoanthraquinones; these, for example 1-aminoanthraquinone, can be converted to numerous valuable vat dyes and light-fast pigments for use in surface coatings.

In the Example which follows, parts are by weight and bear the same relation to parts by volume as that of the gram to the milliliter.

EXAMPLE (a) A mixture of 451.9 parts of vanadium pentoxide, 50.3 parts of ammonium vanadate (NH₄VO₃), 8.0 parts of antimony trioxide and 0.98 part of thallium vanadate (TlVO₃) is suspended in 1,200 parts of water. The suspension (at 20° C.) is conveyed by means of a metering pump to a two-fluid nozzle, where it is finely atomized by means of air introduced for this purpose, and is sprayed, for 25 minutes, onto a loose mass of carrier beads (steatite beads of 6 millimeters diameter, temperature inside the mass 60° C.) contained in a rotating coating dish (angle to the horizontal: 47°, 15 revolutions per minute), with the beads rolling freely under gravity. The rotating dish is ⅝ full. The rate of coating is 0.01 part of solids per part by volume of carrier beads per minute. Some of the water evaporates during the coating process. Drying is then continued for 5 minutes until the temperature in the mass has reached 105° C. The finished catalyst contains 0.15 part of active material per part by volume of carrier. The flame of an oxyacetylene torch is now directed onto the mass, which is at 70° C., for 5 minutes, with the speed and angle of the rotating dish the same as before. The temperature within the mass assumes a value of 630° C. and the surface of the mass is heated to 750° C.; the heating time, and residence time at the heating temperature, of each coated catalyst bead is from 0.1 to 1 second per heating cycle, and cooling requires from 0.1 to 1 second per cooling step for each coated catalyst bead.

(b) 63.72 parts of the catalyst prepared as above are filled into a tubular reactor (21 mm internal diameter). Per hour, a mixture of 200,000 parts by volume of air and 7.6 parts of 1-methyl-3-phenylindan is passed through the catalyst. The tube wall temperature is 420° C. The gaseous reaction mixture leaving the reactor is cooled to 50° C., whereupon the end product and the unconverted 1-methyl-3-phenylindan condense. The uncondensed material is washed with water. After evaporating the wash water, the residue left is combined with the condensate.

The following results are obtained:

| | |
|---|---|
| Starting material 1-methyl-3-phenyl-indan: | 38.10 parts |
| Amount of off-gas: | 1,000,000 parts by volume |
| Content of carbon monoxide and carbon dioxide in the off-gas: | 1.45% by volume |
| Crude end product: | 36.28 parts |

74.1 percent by weight, based on crude end product, of anthraquinone = 26.88 parts are obtained. (This corresponds to a yield of anthraquinone of 70.6% of theory, based on starting material employed).

We claim:

1. A coated catalyst, comprising a non-porous or slightly porous carrier and a layer of catalytic material, containing vanadium compounds, applied thereto, which is obtained by atomizing a mixture of water and a vanadium compound, with or without other metal compounds, and applying this mixture as a coating onto carrier particles which are themselves in constant motion, at from 20° to 90° C. and with a rate of application of from 0.001 to 0.02 part by weight of solids per part by volume of carrier beads per minute, then drying the coated catalysts thus obtained and, by flame heating or plasma heating of the coated catalyst particles which are themselves in constant motion, repeatedly heating all parts of the catalyst surface briefly to above 700° C. and cooling to below 650° C.

2. A process for the preparation of a coated catalyst, comprising a non-porous or slightly porous carrier and a layer of catalytic material, containing vanadium compounds, applied thereto, wherein a mixture of water and a vanadium compound with or without other metal compounds is atomized and this mixture is applied as a coating onto carrier particles which are themselves in constant motion, at from 20° to 90° C. and with a rate of application of from 0.001 to 0.02 part by weight of solids per part by volume of carrier beads per minute, the coated catalysts thus obtained are then dried and all parts of the catalyst surface are repeatedly heated briefly to above 700° C., by flame heating or plasma heating of the coated catalyst particles which are themselves in constant motion, and cooled to below 650° C.

3. Use of a coated catalyst as claimed in claim 1 for the preparation of an anthraquinone by oxidation of an indan of the formula

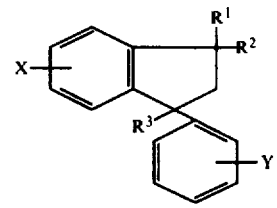

where $R^1$, $R^2$ and $R^3$ may be identical or different and each is alkyl, $R^1$ and/or $R^3$ may in addition also each be hydrogen and X and Y may be identical or different and each is halogen or hydrogen, by means of oxygen in the gas phase in the presence of a vanadium compound and, if desired, one or more compounds of other metals.

4. A process as claimed in claim 2, wherein the catalyst is prepared with vanadium pentoxide and/or vanadates of elements of groups Ia, IIb, IIIa, IIIb, IVa, IVb, Va, Vb, VIa, VIb, VIIb and VIIIb of the periodic table.

5. A process as claimed in claim 2, wherein the catalyst is prepared with an atomic ratio of vanadium to the added elements of group Ia of from 2,000 to 0.5 atom of vanadium per atom of added element, a ratio of vanadium to added elements of group IIIa of from 4,000 to 1 atom of vanadium per atom of added element, a ratio of vanadium to added elements of group IVa of from 2,000 to 0.1 atom of vanadium per atom of added element, a ratio of vanadium to added elements of group Va of from 2,000 to 1 atom of vanadium per atom of added element, a ratio of vanadium to added elements of group VIa of from 2,000 to 1 atom of vanadium per atom of added element, a ratio of vanadium to added elements of group VIIb of from 2,000 to 3 atoms of vanadium per atom of added element, a ratio of vanadium to added elements of group VIIIb of from 100,000 to 0.5 atom of vanadium per atom of added element, a ratio of vanadium to added elements of group IIb of from 2,000 to 3 atoms of vanadium per atom of added element, a ratio of vanadium to added elements of group IIIb of from 2,000 to 1 atom of vanadium per atom of added element, a ratio of vanadium to added elements of group IVb of from 2,000 to 0.1 atom of vanadium per atom of added element, a ratio of vanadium to added elements of group Vb of from 4,000 to 5 atoms of vanadium per atom of added element or a ratio of vanadium to added elements of group VIb of from 2,000 to 4 atoms of vanadium per atom of added element.

6. A process as claimed in claim 2, wherein the catalyst is prepared with sodium aluminum silicate, a magnesium silicate, calcium aluminum silicate, a bleaching earth, a fuller's earth, a clay, kaolin, meerschaum, an allophane, a zeolite, montmorillonite, pumice, Florida earth, quartz, asbestos, mulite, steatite, bentonite, precipitated silica, silica gel, kieselguhr, silicon carbide, corundum, γ-alumina, hydrargillite, boehmite, bauxite, titanium dioxide, zirconium dioxide, tin dioxide, thorium dioxide, magnesite, zinc oxide, mullite, α-alumina, steatite, titanium(IV) oxide or iron(III) oxide as the carrier.

7. A process as claimed in claim 2, wherein the catalyst is prepared with from 0.02 to 0.5 part by weight of catalytic material per part by volume of carrier.

8. A process as claimed in claim 2, wherein the catalyst is prepared using rotating dishes, rotating drums, coating dishes, impregnating drums, coating drums, helical ribbon impellers or mixing vessels as the rotating vessel with a disk-shaped bottom.

9. A process as claimed in claim 2, wherein the catalyst is prepared using a coating dish or rotating dish, with the bottom of the vessel, containing the carrier particles, being at an angle of from 30° to 70° to the horizontal.

10. A process as claimed in claim 2, wherein the catalyst is prepared with the suspension at from 10° to 90° C. during atomizing and with the temperature within the loose mass during application of the active material being from 20° to 90° C.

11. A process as claimed in claim 2, wherein the catalyst is prepared using a rate of application of from 0.001 to 0.02 part by weight of solids per part by volume of carrier beads per minute.

12. A process as claimed in claim 2, wherein the catalyst is prepared in an apparatus which, during coating, is filled to the extent of from 20 to 80 percent by volume with carrier particles, the bottom of the vessel rotating at from 2 to 70 rpm.

13. A process as claimed in claim 2, wherein drying is effected entirely or partially during coating by blowing air or inert gas at from 100° to 300° C. into the loose mass.

14. A process as claimed in claim 2, wherein the catalyst is prepared, in the case of flame heating or plasma heating of the coated catalysts, with the temperature within the loose mass at from 650° to 300° C.

15. A process as claimed in claim 2, wherein the catalyst is prepared, in the case of flame heating or plasma heating of the coated catalyst, with each part (segment) of the surface of each individual coated catalyst particle being brought to from 700° to 3,000° C.

16. A process as claimed in claim 2, wherein the preparation is carried out with from 10 to 1,000 kg of coated catalyst both in the coating step and in the flame or plasma heating step, and with a total treatment time of the coated catalysts by means of the gas torch or plasma torch of from 2 to 60 minutes.

17. A process as claimed in claim 2, wherein the catalyst is prepared, when using a rotating dish, with a diameter of the vessel bottom of from 0.5 to 5 meters, the distance of the torch from the surface of the loose mass being from 2 to 70 centimeters and the flame temperature being from 700° to 2,000° C.

* * * * *